United States Patent [19]

Azer et al.

[11] Patent Number: 4,913,137

[45] Date of Patent: Apr. 3, 1990

[54] INTRAMEDULLARY ROD SYSTEM

[75] Inventors: Samir N. Azer, Alexandria, Va.; Naser N. Salman, Rockville, Md.; William R. Krause, Richmond, Va.

[73] Assignee: Orthopedic Designs, Inc., Alexandria, Va.

[21] Appl. No.: 153,913

[22] Filed: Feb. 9, 1988

[51] Int. Cl.$^4$ .................. A61F 5/04; A61F 2/00
[52] U.S. Cl. ........................... 606/64; 606/65; 606/73; 606/96
[58] Field of Search ....... 128/92 YW, 92 YK, 92 YZ, 128/92 YY, 92 YV, 92 YT, 92 YE, 92 VK, 92 VD

[56] References Cited

U.S. PATENT DOCUMENTS

| D. 282,488 | 2/1986 | Kalen | D24/33 |
|---|---|---|---|
| 2,937,642 | 5/1960 | Lange et al. | 128/92 |
| 3,208,450 | 9/1965 | Abelson | 128/83 |
| 3,759,257 | 9/1973 | Fischer et al. | 128/92 BC |
| 3,892,233 | 7/1975 | Vestby | 128/92 YK |
| 4,055,172 | 10/1977 | Ender et al. | 128/92 BC |
| 4,135,507 | 1/1979 | Harris | f128/92 BC |
| 4,169,470 | 10/1979 | Ender et al. | 128/92 BC |
| 4,281,649 | 8/1981 | Derweduwen | 128/92 BC |
| 4,446,857 | 5/1984 | Otte | 128/92 YK |
| 4,465,065 | 8/1984 | Gotfried | 128/92 BB |
| 4,475,545 | 10/1984 | Ender | 128/92 BC |
| 4,483,335 | 11/1984 | Tornier | 128/92 BC |
| 4,506,662 | 3/1985 | Anapliotis | 128/92 BC |
| 4,519,100 | 5/1985 | Wills | 623/16 |
| 4,530,355 | 7/1985 | Griggs | 128/92 BB |
| 4,561,432 | 12/1985 | Mazor | 128/92 YW |
| 4,574,795 | 3/1986 | Georges | 128/92 BC |
| 4,622,959 | 11/1986 | Marcus | 128/92 YZ |
| 4,667,663 | 5/1987 | Miyata | 128/92 YZ |
| 4,705,027 | 11/1987 | Klaue | 128/92 YY |
| 4,787,378 | 11/1988 | Sodhi | 128/92 YW |

FOREIGN PATENT DOCUMENTS 2166339 4/1971 Fed. Rep. of Germany .
2202051 1/1972 Fed. Rep. of Germany .

OTHER PUBLICATIONS

Biomet, "Interlocking Femoral and Tibial Nails," 3 pp.
Richards Trauma System, "Russell-Taylor Interlocking Nail System," 23 pp.
Synthes, "AO/ASIF Universal Nail: Femoral Nail System," 15 pp.

Primary Examiner—Robert A. Hafer
Assistant Examiner—Michael Brown
Attorney, Agent, or Firm—Fleit, Jacobson, Cohn, Price, Holman & Stern

[57] ABSTRACT

An intramedullary rod system includes a guide rod and a tubular hollow intramedullary rod having an interior surface shaped, at least in a portion, complementary to that of the guide rod. The guide rod is first inserted through the medullary canal and then removed after sliding the tubular intramedullary rod over the guide rod. The guide rod is then aligned outside of the leg parallel to the hollow intramedullary rod for engagement at a distal end by bifurcated prongs with a drill bolt with which bifurcated prongs of the hollow intramedullary rod is simultaneously engaged. Screw holes are thereby aligned between the guide rod and the intramedullary rod at the distal end of the bone without the use of targeting. The hollow intramedullary rod is aligned with the guide rod by a lateral guide for accurate insertion through the guide rod of screws at the distal end of the hollow intramedullary rod.

10 Claims, 4 Drawing Sheets

FIG. 1
FIG. 2
FIG. 3
FIG. 4
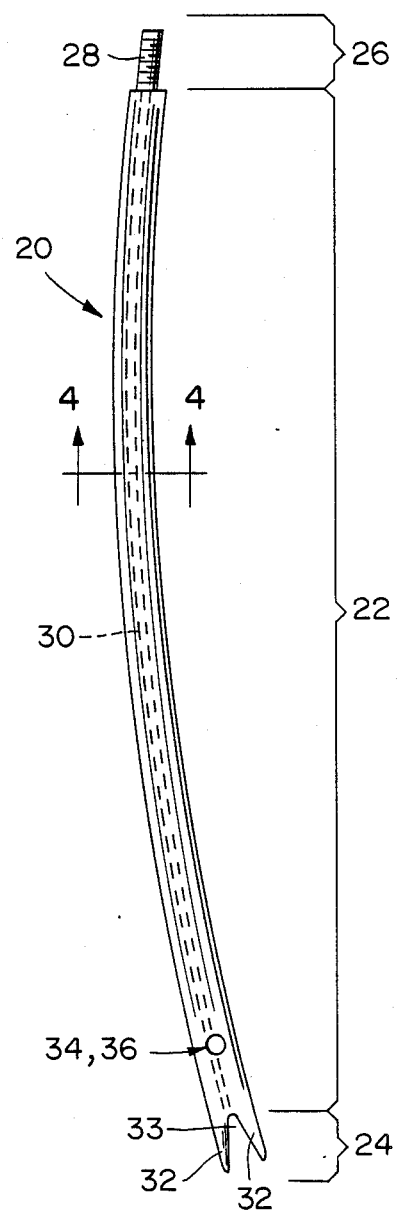
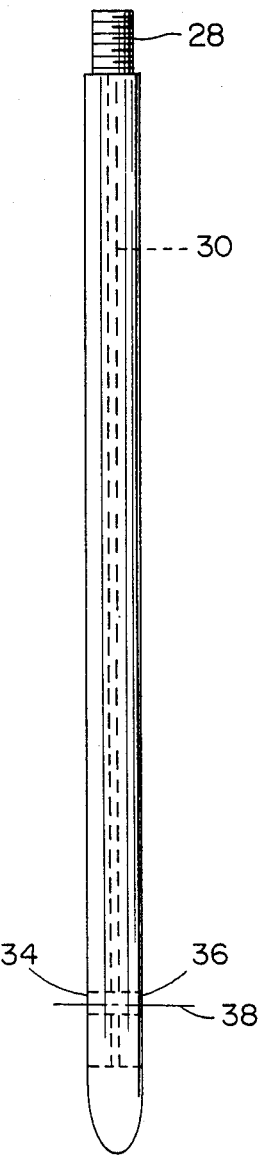
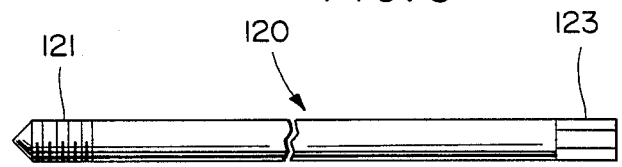
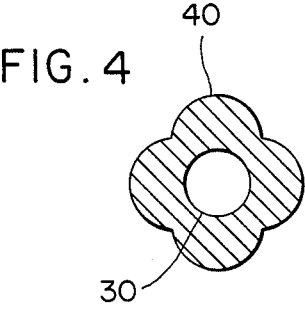

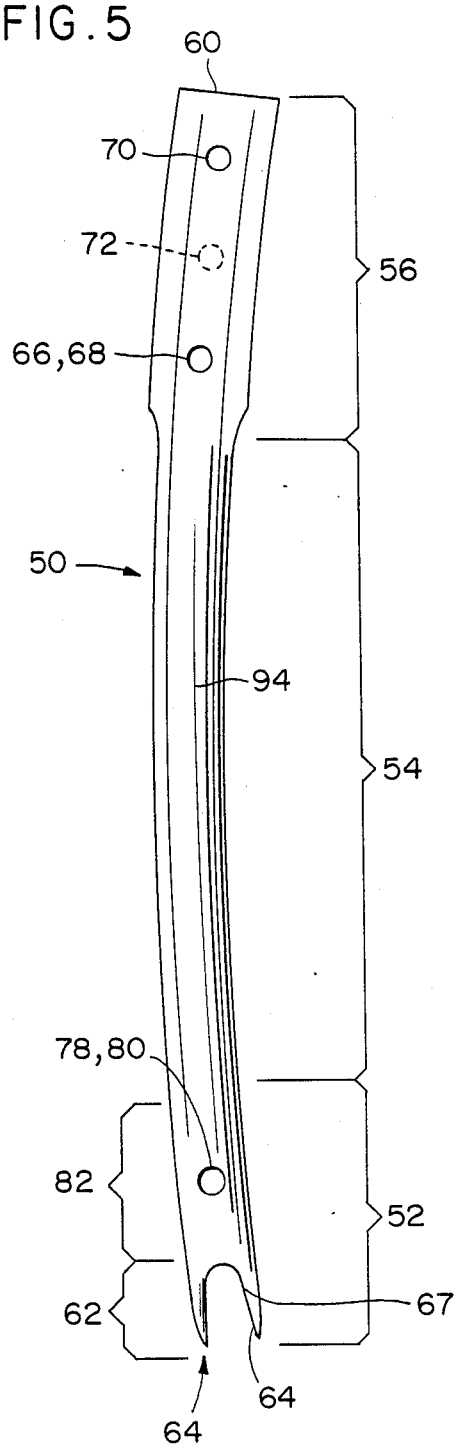
FIG.5
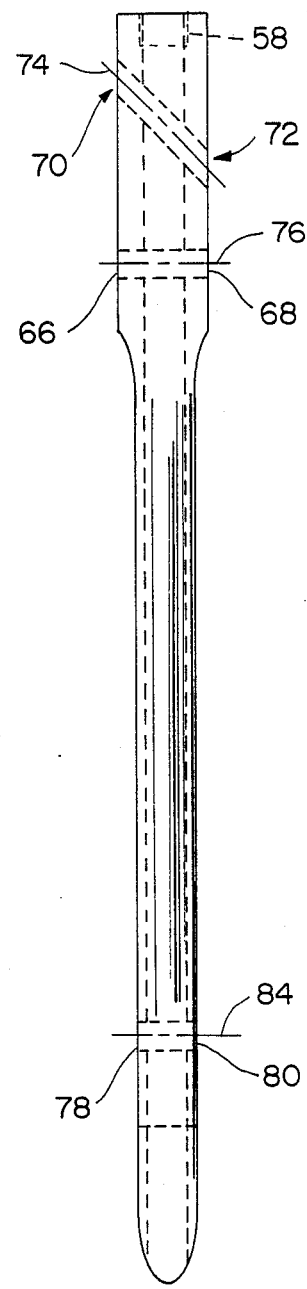
FIG.6
FIG.7

INTRAMEDULLARY ROD SYSTEM

FIELD OF THE INVENTION

This application is directed to an intramedullary system for the fixation of long hollow bones, such as a femur. The system includes a guide rod, a tubular, hollow intramedullary rod and ancillary fixtures for inserting, removing, and fixing the guide rod in place.

BACKGROUND OF THE INVENTION

In the past, methods for the fixation of fractured long hollow bones involved the use of a bone plate with screw holes to which all the pieces of a fractured bone were secured. However, such procedures required large operative openings which increased the risk of infection. Further, it was necessary to remove the metal bone plates after several years, since the holes through which the bone nails passed weakened the bone and caused the bone plate to absorb stress on the leg.

The shortcomings of using bone plates led to the development of a semi-invasive method for external fixation of pins through the skin to connect bone to an intramedullary rod. This procedure required a 2-inch incision through which a guidewire was passed for insertion of an open, channeled, intramedullary rod to which the pieces of bone were connected. While this approach reduced operating time and placed the pieces of bone in better alignment, it was eventually discovered that this method did not prevent the intramedullary rod from rotating during walking and other movement of the leg.

U.S. Pat. No. 4,519,100 to Wills et al. attempted to overcome the problems caused by rotation of an intramedullary rod by using a plurality of pivotable blades which rotate outwardly to engage the distal end of a fractured bone. In this method, the blades are pivotably coupled to a connector member, which translates longitudinally in either direction within an elongated shaft. Translation of the connector member towards the front end of a covering sheath resulted in the outward rotation of the blades into the bone at its distal end. With the device inserted lengthwise into the bone, the bone-engaging mechanism was supposed to prevent rotation, angulation, and antero-posterior translation. However, a longitudinal track defined along the entire length of the covering sheath has been found to cause loss of torsional rigidity. In addition, problems have been encountered with deployment of the engagement fins.

One method which seeks to overcome these problems is the Russell-Taylor interlocking nail system, in which screws are placed at both ends of an open channeled, cloverleaf-shaped Kirchner rod. It has been found that when this type of rod is put in a circular medullary canal, compression results on three points of the rod, causing the bone to resorb and allowing the rod to rotate.

According to the Russell-Taylor interlocking nail system, an oblique skin incision is made 2 cm distal to the proximal tip of the greater trochanter and continued proximally and medially for 8-10 centimeters. The fascia of the gluteous maximus is incised in line with the skin incision.

A curved awl, designed to enlarge the entry portal, is introduced at the trochantric fossa in line with the femoral shaft. The blunt tip of a tapered T-handle reamer is used to enlarge the metaphyseal canal.

A ball-tip guide rod is introduced into the bone to the level of the fracture. Containment of the guide rod within the femur is confirmed by antero-posterior and lateral image intensification. After reaming of the proxima femur, an alignment device is inserted.

A guide pin is extended into the distal fragment until the tip reaches the old epiphyseal scar or distal pole of the patella, after which the alignment device is removed. Containment of the guide rod within the femur is verified by image intensification. A C-arm is used to determine a proper length with a nail length gauge.

A medullary alignment tube is introduced over the guide rod to maintain fracture reduction. The ball-tip guide rod is replaced with a nail guide rod, and then the medullary alignment tube is removed.

A locking nail is entered into the distal fragment by several centimeters through a proximal drill guide. The nail is then driven so that the proximal end is flush with the tip of the greater trochanter. For distal attachment, a distal incision is made immediately before the distal "targeting" procedure. An image intensifier is used to assist in locating the nail holes in the locking nail. The holes should appear as perfect circles for proper alignment of distal bone fragment nails.

The use of a fluoroscope or image intensifier used in this and other procedures is made to assure alignment of the screws with the inserted rods (targeting). A surgeon views the intended area of placement of a screw and places his or her hands in the field of view to position a screw with respect to a drilled hole. This method has raised the concern of repeated exposure to small doses of radiation, which may be cumulative in affecting a surgeon's health over time.

Another method of use of a femoral nail system is described in a brochure entitled "AO/ASIF Universal Nail," by Synthes.

In U.S. Pat. No. 4,622,959 to Marcus, an intramedullary nail is described for use in repairing fractures of the left or right femur. The nail includes a body having a head, an intermediate portion, and a distal tip. Transverse openings are provided in the body near the distal tip and in the head for receiving locking screws. One opening in the head has its axis within the femoral neck, and another opening has its axis generally transverse thereto. The proximal nail head has a seat with a transverse locating slot for securing a screw insertion tool in a fixed angular position. A screw guide on the tool is aligned with one of the screw-receiving openings.

By the method and apparatus of the present invention, the problems encountered with the previously known procedures have been overcome.

SUMMARY OF THE INVENTION

According to the method of the invention, a guidewire is first inserted toward a distal end of a bone. A hollow reamer is inserted over the guidewire to ream out a opening 1-2 mm greater than the size of the intramedullary rod to be permanently located in the bone.

After removal of the guidewire and reamer, a hole is drilled into the distal end of the bone in a direction transverse to the reamed medullary canal. A trans-cortical pin long enough to project laterally from the leg is then inserted into the drilled hole.

A four-sided closed cloverleaf configured guide rod is then inserted into the reamed hole which extends longitudinally along the bone. The end of the guide rod is bifurcated into two prongs to receive and lock the position of the guide rod with the trans-cortical pin.

The trans-cortical pin is engaged by the deepest portion of the longitudinal channel extending between the bifurcated distal end of the guide rod. A pair of holes is located proximally to the end of the channel created by the anterior and posterior prongs. The axis of this pair of holes are coaxially arranged on a common axis passing through the guide rod in transverse relation to the longitudinal direction of the guide rod and in parallel to the axis of the proximal end of the channel.

A tubular hollow intramedullary rod is then slid over the guide rod. The hollow intramedullary rod has a distal end in a circular configuration, a mid-portion of a cloverleaf configuration complementary to that of the guide rod, and a proximal end of a hexagonal configuration. The distal end of the hollow intramedullary rod is bifurcated into two prongs similar to that of the guide rod to similarly engage the drill bit. The similarly configured portion of the hollow intramedullary rod to that of the guide rod prevents twisting of the hollow intramedullary rod relative to the guide rod.

The proximal portion of the hollow intramedullary rod is provided with two pairs of holes or openings. A pair of holes is located at the distal end of the intramedullary rod spaced the same distance from the distal tips of the prongs as is a pair of holes of the guide rod spaced from the distal tips of its prongs. The axes of the proximal portion holes of the hollow intramedullary rod are located in a common plane extending substantially in a normal direction to the anterior-posterior prongs plane. The most proximal pair of holes of the two pair of proximal holes have their axis at a 45° angle to the longitudinal axis of the tubular hollow intramedullary rod, with the lateral hole being more proximal than the medial hole. The second pair of proximal holes is more distal than the first pair and has its axis oriented perpendicular to the longitudinal axis in the medial-lateral plane of the intramedullary rod.

After the hollow intramedullary rod is positioned in engagement with the trans-cortical pin, the guide rod is withdrawn. A slot defined at the proximal end of the hollow medullary rod receives a nail insert. One end of the nail insert is anchored to the hollow intramedullary rod, whereas another portion of the nail insert engages a lateral guide connected to the previously withdrawn guide rod, which now extends parallel to and spaced from the hollow intramedullary rod. The bifurcated distal end of the guide rod engages outside of the leg the same trans-cortical pin as is engaged by the hollow tubular intramedullary rod within the medullary canal.

The guide rod provides an exact alignment between holes located in the hollow intramedullary rod and guide rod such that the fitting of a trans-cortical pin through the distal openings of the externally positioned guide rod will be aligned to pass through the distal openings of the hollow intramedullary rod. Bone screws are thereby accurately positioned within the leg.

It is an object of the present invention to provide an intramedullary rod system including a guide rod and a tubular hollow intramedullary rod.

It is another object of the present invention to provide an intramedullary rod system including a guide rod and a tubular hollow intramedullary rod with an interior surface shaped, at least in a portion, complementary to that of the guide rod, which is first inserted through the medullary canal and then removed after sliding the tubular intramedullary rod over the guide rod.

It is a further object of the present invention to provide an intramedullary rod including a guide rod and a tubular hollow intramedullary rod having an interior surface shaped, at least in a portion, complementary to that of the guide rod, which is first inserted through the medullary canal and then removed after sliding the tubular intramedullary rod over the guide rod and the guide rod being aligned parallel to the hollow, intramedullary rod for engagement at a distal end with a trans-cortical pin with which the hollow intramedullary rod is simultaneously engaged for aligning of screw holes.

It is yet another object of the present invention to provide an intramedullary rod system including a guide rod and a tubular hollow intramedullary rod having an interior surface shaped, at least in a portion, complementary to that of a guide rod, which is first inserted through the medullary canal and then removed after sliding the tubular intramedullary rod over the guide rod and the guide rod being aligned parallel to the hollow intramedullary rod for engagement at a distal end with a trans-cortical pin with which the hollow intramedullary rod is simultaneously engaged for aligning of screw holes, the hollow intramedullary rod being aligned with the guide rod by a lateral guide for accurate insertion through the guide rod of the screws at the distal end of the hollow in intramedullary rod.

These and other objects of the invention, as well as many of the intended advantages thereof, become more readily apparent with reference to the following description, taken in conjunction with the accompanying drawings.

BRIEF DESCRIPTION OF THE DRAWINGS

In the annexed drawings, the invention is schematically illustrated with reference to a preferred embodiment.

FIG. 1 shows a side elevation (lateral view) of the guide rod designed according to the invention.

FIG. 2 shows a front elevation (anterior view) of the guide rod shown in FIG. 1.

FIG. 3 is a side elevational view of a trans-cortical pin shown in FIG. 15.

FIG. 4 is a sectional view taken along line 4—4 of FIG. 1.

FIG. 5 shows a side elevation (lateral view) of the intramedullary rod for a femur designed according to the invention.

FIG. 6 shows a front elevation (anterior view) of the intramedullary rod.

FIG. 7 is a side elevation of the intramedullary rod, opposite to that shown in FIG. 5, shown in a straight condition for purposes of illustration only.

DETAILED DESCRIPTION OF THE PREFERRED EMBODIMENT

Figure 10:
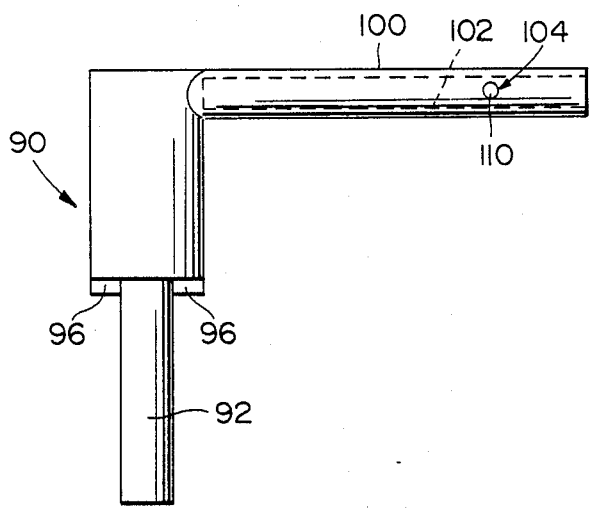
FIG. 10 is a side view of a nail insert.
Figure 11:
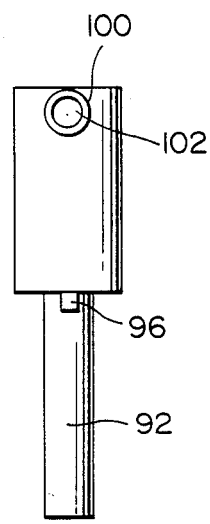
FIG. 11 is an end view of the nail insert shown in FIG. 10.
Figure 12:
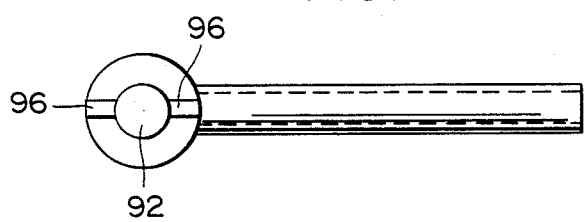
FIG. 12 is a bottom view of the nail insert shown in FIG. 10.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings in general, and to FIGS. 1 through 4 in particular, a guide rod embodying the teachings of the subject invention is generally designated as 20. The intramedullary rod shown in the drawings and intended for the treatment of a fracture to the femur includes a tubular and curved base portion 22 when located in a medullary canal. A distal portion 24 is located at the distal end of the base portion 22. At the opposite end is a proximal portion 26. All three portions are of a closed, tubular cross-section shaped in a four-sided cloverleaf configuration, as shown in FIG. 4.

The proximal portion 26 includes a threaded portion 28 for coupling with additional instruments for use in driving, extracting, and inserting the guide rod. The proximal, base, and distal portions are cannulated, as shown by cannula opening 30, for passage of a 4 mm guide pin. The proximal portion 26 is threaded to threadingly engage with a driving device or other ancillary instruments for insertion or removal. The distal portion 24 is bifurcated into prongs 32, which define longitudinal channel 33. The bifurcation is intended to engage a trans-cortical pin placed across the distal femur portion.

A pair of holes 34, 36 are located proximal to the proximal end of the prongs 32. The holes 32, 34 are used for drilling a hole through the bone and into and through an inserted intramedullary rod. The axis 38 of the holes 34, 36 is located in the medial-lateral direction, transverse and perpendicular to the longitudinal axis of the guide rod 20.

In FIG. 1, the guide rod 20 includes a slight curvature which closely resembles that of a femur.

In FIGS. 5 through 9, intramedullary rod 50 is shown. The intramedullary rod 50 has a curvature substantially following that of the guide rod shown in FIG. 1 and the femur. FIG. 7 illustrates the intramedullary rod in a straight condition for illustrative purposes only. Normally, this rod is curved.

The intramedullary rod shown in the drawings is intended for the treatment of a fracture of the femur. The rod 50 is hollow and tubular having a distal tip portion 52, a central portion 54, and a proximal portion 56. All three portions are of a closed, tubular cross-section.

The proximal portion 56 includes an internal threaded section 58 for coupling with additional instrumentation and for driving, extracting, and inserting alignment devices. In addition, a transverse groove 60 accepts a complementary shape projection of an alignment device to extend from the intramedullary rod.

Figure 8:
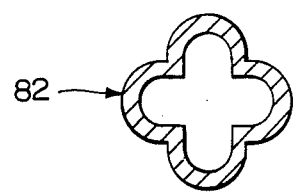
FIG. 8 is a sectional view taken along line 8—8 of FIG. 7.
Figure 16:
FIG. 16 shows the intramedullary rod anchored in a femur or thigh bone as viewed from the front (anterior view).
Figure 9:
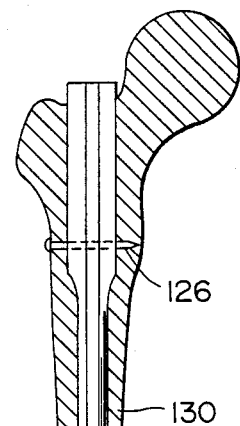
FIG. 9 is an end view taken along line 9—9 of FIG. 7.
Figure 9:
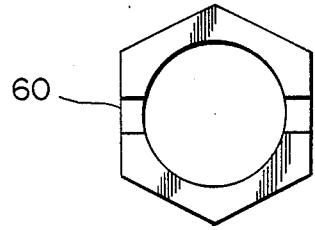

The central portion 54 has an internal cross-section, as shown in FIG. 8, which is complementary to the external configuration of the guide rod 20. A cloverleaf external configuration 82 is shown for illustration purposes. However, this configuration may be changed as long as the external configuration and the internal configuration of the guide rod and intramedullary rod, respectively, are complementary and are dimensioned to prevent turning of one of the guide rod and intramedullary rod with respect to the other. The external configuration of the rod 50 allows for increased endosteal blood supply to the fracture site by the flow of blood around the indented areas between adjacent curved portions of the cloverleaf.

The distal portion 52 is of a circular tubular cross-section, with a bifurcated end 62, which includes prongs 64. A longitudinal channel 66 extends proximally from the tip of the prongs 64 along the medial and lateral aspects of the rod.

Pairs of holes 66, 68 and 70, 72 are located in the proximal portion 56. Screws can be passed through the respective pairs of holes for anchoring the rod 50 to the proximal bone fragment 130. The screws prevent rotation of the bone with respect to the rod. The most proximal pair of holes 70, 72 are located along an axis 74, which extends at a 45° angle with respect to the longitudinal axis of the rod. The most distal hole 72 of the pair is located on the medial aspect of the rod. The distal pair of holes 66, 68 are located distally from the pair of holes 70, 72, and its axis 76 is located perpendicular to the longitudinal axis of the rod in a transverse, medial-lateral direction.

A single pair of holes 78, 80 are located in a proximal area 78 of distal portion 52. Section 82 is located proximally to the most proximal portion of the channel 67. The axis 84 of the pair of holes 78, 80 is situated in the medial-lateral direction transverse and perpendicular to the longitudinal axis of the rod.

The longitudinal channel 67 divides the most distal region 62 into bifurcated prongs 64. Longitudinal channel 67 is used to engage a trans-cortical pin 120, shown in FIG. 3, driven across the bone prior to insertion of the guide rod. The slot is tapered to align the guide rod, and subsequently the intramedullary rod, with respect to the inserted drill bolt 120.

The use of the guide and intramedullary rods, as used towards reduction of a femur, will now be described. Reduction is the restoration of a fractured bone to a normal anatomic relationship.

A patient is first placed in either the lateral or supine position on a fracture table. Skeletal traction is applied through a previously placed femoral pin. Reduction of the fracture is thereby achieved. The accurate reduction of the bone is verified by x-ray monitoring. X-ray monitoring allows the surgeon to view the surgical site without exposing his or her hands at the site being irradiated with x-rays.

When proper reduction has been verified, a 10 cm incision is made, starting at the greater trochanter and extending proximally along the gluteal fibres. By muscle splitting, the pyriformis fossa is palpated.

The medullary canal is then opened with an awl. The positioning of the awl is verified by x-ray monitoring.

A sharp, pointed reamer rod is then passed through the opened medullary canal and passed across the fracture site. The reamer rod may be bent at the tip to allow passage through the distal fragment. The reamer rod is advanced to the level of the intercondylar notch. The positioning of the reamer rod is confirmed by x-ray monitoring.

A polyethylene tube is then passed over the sharp, pointed reamer rod. The reamer rod is extracted and replaced with a ball-tip reamer rod. The polyethylene tube is then removed.

Reaming is begun over the ball-tip reamer rod, starting with a 9 mm flexible reamer. Reaming progresses at 0.5 mm increments. Reaming continues until the appropriate diameter is achieved and stops when passing through a comminuted fracture area. At this point, the polyethylene tube is again inserted over the ball-tip reamer rod. The ball-tip reamer rod is then extracted and replaced with a calibrated guide rod.

A 2 cm incision is then made in the lateral distal thigh. Using a drill sleeve, the lateral femoral cortex is located. The sleeve is placed at right angles to the femur and at the midpoint between the anterior and posterior cortices using an especially designed jig. A drill bolt is then drilled through the drill sleeve to puncture the lateral and medial cortices. The drill sleeve is then removed, and the drill bolt is left in place. The drill bolt 120 includes cutting tap head 121 and head 123.

A guide rod, as shown in FIGS. 1 through 3, having a diameter approximately 5 mm smaller than the medullary canal is selected. The guide rod is then inserted over the calibrated guide rod. Free rotation and easy passage of the guide rod is assured, since it is smaller than the medullary canal. The bifurcation at the distal tip of the guide rod allows easy passage across the fracture site. Once the guide rod passes the fracture site, as determined by x-ray monitoring, the calibrated guide rod is extracted.

The guide rod is advanced, and the prongs of its distal bifurcation are allowed to center the drill bolt into the longitudinal channel formed between the prongs. This is achieved with minimal rotation of the guide rod. Confirmation of the axilla of the guide rod fully engaging the drill bolt is done by x-ray monitoring.

An appropriately sized intramedullary rod, as previously determined through a reading of the calibrated guide rod, is inserted in the intramedullary canal. The diameter of the intramedullary rod is 1 mm smaller than the last largest reamer. The appropriately sized intramedullary rod is then passed over the guide rod. The cloverleaf configuration of the intramedullary rod corresponds to the exterior configuration of the guide rod, thus eliminating any possibility of medullary rod rotation. The distal bifurcation of the intramedullary rod is thereby also aligned with that of the guide rod to engage the drill bolt 120. Full engagement of the intramedullary rod distal bifurcation against the drill bolt is confirmed by x-ray monitoring. The guide rod is then withdrawn.

Figure 15:
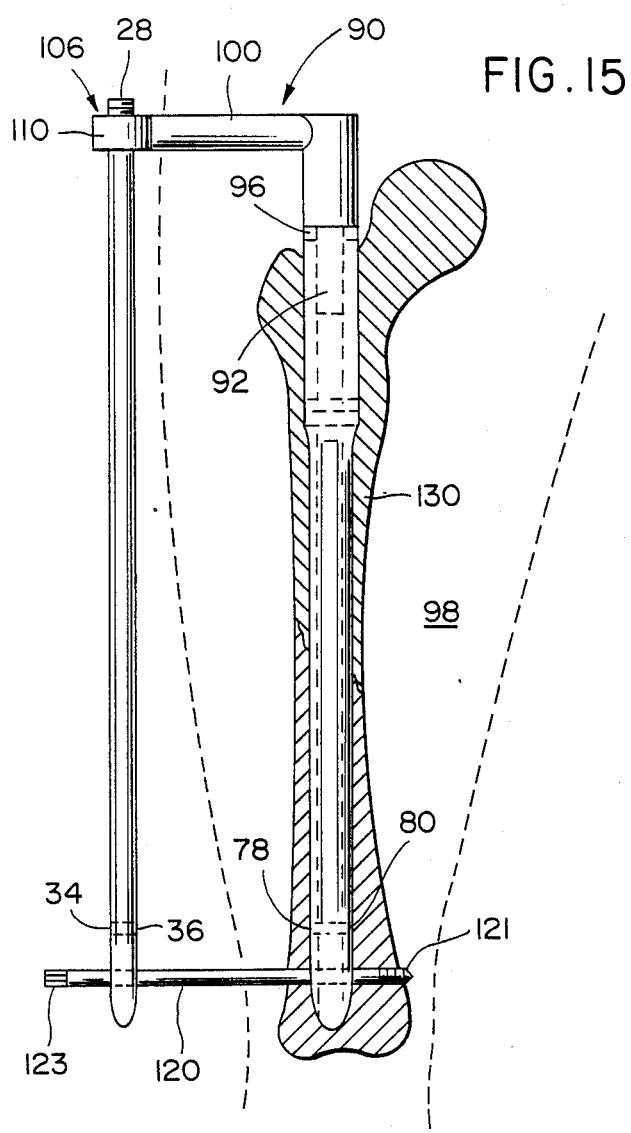
FIG. 15 is a side sectional view of an inserted medullary rod and guide rod interconnected by a nail insert and lateral guide.

Nail insert 90, as shown in FIG. 10, is then mounted onto the proximal end of the intramedullary rod. Center shaft 92 slides within channel 94 of the intramedullary rod. Projecting fins 96 are located in grooves 60 of the proximal end of the intramedullary rod. Nail insert 90 thereby projects laterally from the thigh 98 of the patient, as shown in FIG. 15, by lateral extension 100, which includes central channel 102 with set screw hole 104. Lateral extension 100 is hollow and projects beyond the skin surface of thigh 98.

Figure 13:
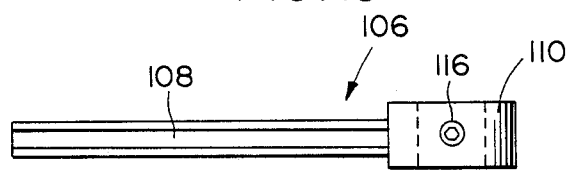
FIG. 13 is a side view of a lateral guide.
Figure 14:
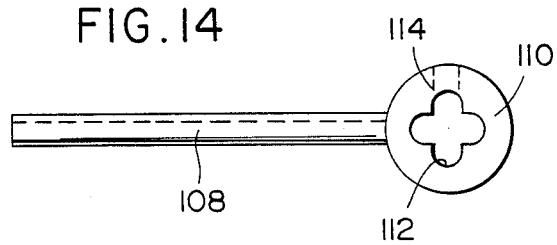
FIG. 14 is a top plan view of the lateral guide shown in FIG. 13.

Lateral guide 106, as shown in FIGS. 13 and 14, includes lateral projection 108, which fits within channel 102 of nail insert 90. Set screw 110 is tightened against projection 108 to lock the projection in place within channel 102. Lateral extension 100, projection 108, and drill bolt 120 are calibrated so as to accurately position the guide rod with respect to the intramedullary rod in a parallel relationship. Parallelism between the guide rod and the, intramedullary rod assures accurate alignment of a drill through the distal holes of the guide rod into the distal holes of the intramedullary rod.

Clamping sleeve 110 is located at one end of the projection 108. Clamping sleeve 110 includes a cloverleaf-shaped opening 112, through which the guide rod is intended to pass. The shape of the opening 112 is complementary to that of the guide rod. A set screw channel 114 allows for tightening of a set screw 116 against the guide rod. The guide rod is passed through the clamping sleeve of the lateral guide and, due to the shape of opening 112, complementary to that of the guide rod, eliminates the possibility of the guide rod rotating.

The guide rod which was previously used to align the intramedullary rod within the medullary canal is advanced to engage the portion of the drill bolt 120 which extends laterally from the thigh. The guide rod is advanced until the axilla of the bifurcated prongs 32 fully engages the drill bit 120. This thereby automatically aligns the distal interlocking hole 34, 36 of the guide rod, with the corresponding hole 78, 80 in the intramedullary rod.

A drill sleeve is then passed through the opening 34, 36 of the guide rod. A stab wound is made in the lateral thigh at that site. The drill sleeve is advanced to the lateral cortex of the femur. The drill bit is then drilled through the lateral cortex, through the intramedullary rod, and into the medial cortex. The nail insert, lateral guide, and guide rod are then removed. A screw 122 is then inserted and screwed in the distal femur.

The drill bolt 120 extending through the bifurcated ends of the guide rod and medullary rod is then removed. A depth gauge is used to measure the appropriate size screw. A distal screw 124 is then inserted into the bone in the place previously occupied by drill bit 120, which is confirmed by x-ray monitoring. A known procedure not forming part of the invention is used for insertion of a proximal screw 126.

By the present invention, the distal screws for a distal bone fragment are accurately inserted. Previous techniques have required the use of targeting, which requires that the surgeon view the targeted area and exposure to his or her hands and body to radiation for extended periods of time while being at the irradiated site. By use of the guide rod and intramedullary rod of the invention, x-ray monitoring to confirm proper placement of bone screws is done by viewing the work site from a safe distance. Therefore, the surgeon is not exposed to radiation during the implantation operation.

Having described the invention, many modifications thereto will become apparent to those skilled in the art to which it pertains, without deviating from the spirit of the invention, as defined by the scope of the appended claims.

We claim:

1. An intramedullary rod system comprising:
a guide rod for insertion into a medullary canal,
an intramedullary rod for insertion into the medullary canal around said guide rod,
an interior surface of said intramedullary rod being shaped and fitted complementary to an exterior surface of said guide rod and preventing rotation of said intramedullary rod with respect to said guide rod, and
alignment means for aligning said guide rod parallel to and spaced from said intramedullary rod after said guide rod has been withdrawn from inside said intramedullary rod, said guide rod and said intramedullary rod being aligned with respect to each other to position and axis of distal openings in said guide rod along an axis of distal openings in said intramedullary rod.

2. An intramedullary rod system according to claim 1, wherein a distal end of said guide rod and a distal end of said intramedullary rod are bifurcated to each define a longitudinal channel.

3. An intramedullary rod system according to claim 2, wherein said guide rod and said intramedullary rod engage a bolt means of said alignment means at a base of their respective longitudinal channels for positioning said intramedullary rod and said guide rod with respect to each other.

4. An intramedullary rod system according to claim 3, wherein said alignment means includes guide means for aligning a proximal end of said guide rod and a proximal end of said intramedullary rod with respect to each other.

5. An intramedullary rod system comprising:
a guide rod having a distal end and a proximal end, said distal end being bifurcated to define a longitudinal channel and said distal end includes an opening extending through said distal end having an axis extending transverse to a longitudinal axis of said guide rod,
an intramedullary rod being hollow and having a distal end and a proximal end, said distal end being bifurcated to define a longitudinal channel and said distal end including an opening extending through said distal end having an axis extending transverse to a longitudinal axis of said guide rod,
said axis of said opening of said guide rod being spaced a distance from a base of said longitudinal channel of said guide rod equal to a distance of said axis of said opening of said intramedullary rod spaced from a base of said longitudinal channel of said intramedullary rod, and
an interior surface of said hollow intramedullary rod being shaped and fitted complementary to an exterior surface of said guide rod, said exterior surface being configured so as to prevent rotation of said intramedullary rod with respect to said guide rod when said intramedullary rod surrounds said guide rod.

6. An intramedullary rod system according to claim 5, further comprising rod means engaged by said base of said longitudinal channel of said guide rod and said base of longitudinal channel of said intramedullary rod when said guide is aligned spaced from said intramedullary rod for aligning said opening of said guide rod with said opening of said intramedullary rod.

7. An intramedullary rod system according to claim 6, further comprising guide means for spacing said proximal end of said guide rod from said proximal end of said intramedullary rod so as to align, in combination with said bolt means, said guide rod and said intramedullary rod parallel to each other.

8. An intramedullary rod system comprising:
a guide rod having a distal end and a proximal end,
an intramedullary rod having a distal end and a proximal end,
guide means defined by said distal end of said guide rod and said distal end of said intramedullary rod, and
alignment means for locating along the same axis, an axis of an opening defined by said guide rod and an axis of an opening defined by said intramedullary rod, said guide means including a bifurcation located at said distal end of said guide rod and said distal end of said intramedullary rod.

9. An intramedullary rod system according to claim 8, wherein an interior surface of said intramedullary rod is shaped complementary to an exterior surface of said guide rod, said exterior surface being configured so as to prevent rotation of said intramedullary rod with respect to said guide rod when said intramedullary rod surrounds said guide rod.

10. An intramedullary rod system according to claim 9, wherein said alignment means includes a bolt means engaged by said distal end of said guide rod and said distal end of said intramedullary rod and lateral guide means engaged by said proximal end of said guide rod and said proximal end of said intramedullary rod.

* * * * *